(12) United States Patent
Wilkinson et al.

(10) Patent No.: US 10,279,280 B2
(45) Date of Patent: May 7, 2019

(54) PROCESS AND APPARATUS FOR THE PREPARATION OF ALKYLENE GLYCOL

(71) Applicant: SHELL OIL COMPANY, Houston, TX (US)

(72) Inventors: Peter Mervyn Wilkinson, Amsterdam (NL); Jesse Raymond Black, Katy, TX (US); Roel Guillaume Hubertus Leonardus Bastings, Amsterdam (NL)

(73) Assignee: SHELL OIL COMPANY, Houston, TX (US)

(*) Notice: Subject to any disclaimer, the term of this patent is extended or adjusted under 35 U.S.C. 154(b) by 0 days.

(21) Appl. No.: 15/513,572

(22) PCT Filed: Sep. 21, 2015

(86) PCT No.: PCT/EP2015/071534
§ 371 (c)(1),
(2) Date: Mar. 23, 2017

(87) PCT Pub. No.: WO2016/046100
PCT Pub. Date: Mar. 31, 2016

(65) Prior Publication Data
US 2017/0291119 A1    Oct. 12, 2017

(30) Foreign Application Priority Data
Sep. 24, 2014 (EP) .................... 14186273

(51) Int. Cl.
| C07C 31/20 | (2006.01) |
| B01D 3/20 | (2006.01) |
| B01D 3/22 | (2006.01) |
| C07C 29/10 | (2006.01) |

(52) U.S. Cl.
CPC .............. B01D 3/20 (2013.01); B01D 3/22 (2013.01); C07C 29/106 (2013.01); C07C 31/202 (2013.01)

(58) Field of Classification Search
None
See application file for complete search history.

(56) References Cited

U.S. PATENT DOCUMENTS

| 4,435,595 A | 3/1984 | Agreda et al. |
| 2010/0094065 A1 | 4/2010 | Slapak |
| 2013/0231501 A1 | 9/2013 | Hasselbach et al. |
| 2013/0245318 A1 | 9/2013 | Steffan et al. |

FOREIGN PATENT DOCUMENTS

| CN | 102219642 A | 10/2011 |
| EP | 0542538 | 5/1993 |
| EP | 776890 | 1/2001 |
| EP | 1964829 | 9/2008 |
| GB | 2107712 | 5/1983 |
| WO | 2009021830 | 2/2009 |

OTHER PUBLICATIONS

International Search Report dated Oct. 19, 2015 for SP0419—3 pages.
International Search Report and Written Opinion received for PCT Patent Application No. PCT/EP2015/071534, dated Oct. 28, 2015, 9 pages.

*Primary Examiner* — Ana Z Muresan

(57) ABSTRACT

A process for the preparation of an alkylene glycol from an alkene is provided, along with an absorber apparatus. The process comprises: supplying a gas composition to an absorber comprising a column of vertically stacked trays, wherein each of the vertically stacked trays comprises: a perforated gas-liquid contacting member or members, a liquid inlet area, an outlet weir extending vertically above a surface of the tray at an opposite end of the tray from the liquid inlet area and having a height of at least 200 mm and at most 1500 mm, and a downcomer element which, in cooperation with an inner surface of a wall of the column, forms a downcomer for the passage of liquid downwardly to the liquid inlet area of an adjacent vertically stacked tray below, and allowing the gas composition to pass upwards through the alkylene oxide absorber.

5 Claims, 1 Drawing Sheet

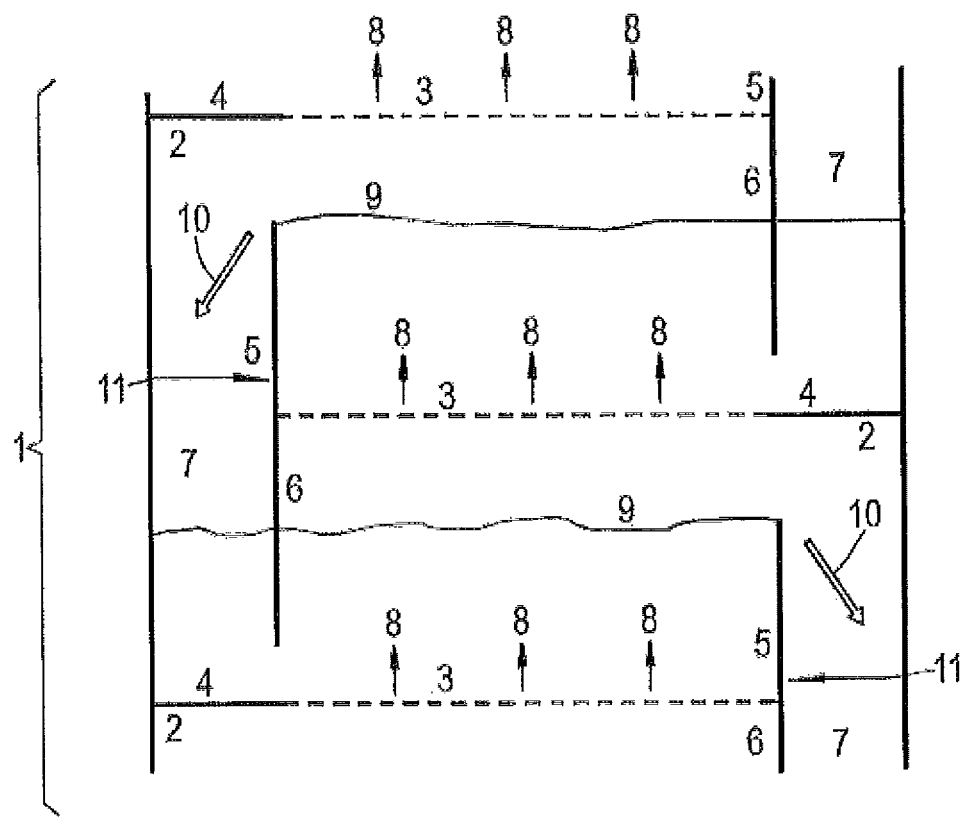

PROCESS AND APPARATUS FOR THE PREPARATION OF ALKYLENE GLYCOL

PRIORITY CLAIM

The present application is the National Stage (§ 371) of International Application No. PCT/EP2015/071534, filed Sep. 21, 2015, which claims priority from European Patent No. 14186273.0, filed Sep. 24, 2014 incorporated herein by reference.

FIELD OF THE INVENTION

The present invention relates to a process and an apparatus for the preparation of an alkylene glycol from the corresponding alkene.

BACKGROUND OF THE INVENTION

Monoethylene glycol is used as a raw material in the manufacture of polyester fibres, polyethylene terephthalate (PET) plastics and resins. It is also incorporated into automobile antifreeze liquids.

Monoethylene glycol is typically prepared from ethylene oxide, which is in turn prepared from ethylene. Ethylene and oxygen are passed over a silver oxide catalyst, typically at pressures of 10-30 bar and temperatures of 200-300° C., producing a product stream comprising ethylene oxide, carbon dioxide, ethylene, oxygen and water. The amount of ethylene oxide in the product stream is usually between about 0.5 and 10 weight percent. The product stream is supplied to an ethylene oxide absorber and the ethylene oxide is absorbed by a re-circulating solvent stream containing mostly water. The ethylene oxide-depleted stream is partially or entirely supplied to a carbon dioxide absorption column wherein the carbon dioxide is at least partially absorbed by a re-circulating absorbent stream. Gases that are not absorbed by the re-circulating absorbent stream are recombined with any gases bypassing the carbon dioxide absorption column and are recycled to the ethylene oxide reactor.

The solvent stream leaving the ethylene oxide absorber is referred to as fat absorbent. The fat absorbent is supplied to an ethylene oxide stripper, wherein ethylene oxide is removed from the fat absorbent as a vapour stream. The ethylene oxide-depleted solvent stream is referred to as lean absorbent and is recirculated to the ethylene oxide absorber to absorb further ethylene oxide.

The ethylene oxide obtained from the ethylene oxide stripper can be purified for storage and sale or can be further reacted to provide ethylene glycol. In one well-known process, ethylene oxide is reacted with a large excess of water in a non-catalytic process. This reaction typically produces a glycol product stream consisting of almost 90 weight percent monoethylene glycol, the remainder being predominantly diethylene glycol, some triethylene glycol and a small amount of higher homologues. In another well-known process, ethylene oxide is catalytically reacted with carbon dioxide to produce ethylene carbonate. The ethylene carbonate is subsequently hydrolysed to provide ethylene glycol. Reaction via ethylene carbonate significantly improves the selectivity of ethylene oxide conversion to monoethylene glycol.

Efforts have been made to simplify the process for obtaining ethylene glycol from ethylene, reducing the equipment that is required and reducing the energy consumption. GB 2107712 describes a process for preparing monoethylene glycol wherein the gases from the ethylene oxide reactor are supplied directly to a reactor wherein ethylene oxide is converted to ethylene carbonate or to a mixture of ethylene glycol and ethylene carbonate.

EP 776890 describes a process wherein the gases from the ethylene oxide reactor are supplied to an absorber wherein the absorbing solution mainly contains ethylene carbonate and ethylene glycol. The ethylene oxide in the absorbing solution is supplied to a carboxylation reactor and allowed to react with carbon dioxide in the presence of a carboxylation catalyst. The ethylene carbonate in the absorbing solution is subsequently supplied, with the addition of water, to a hydrolysis reactor and subjected to hydrolysis in the presence of a hydrolysis catalyst.

EP 2178815 describes a reactive absorption process for preparing monoethylene glycol wherein the gases from the ethylene oxide reactor are supplied to an absorber and the ethylene oxide is contacted with lean absorbent comprising at least 20 wt % water in the presence of one or more catalysts that promote carboxylation and hydrolysis and the majority of the ethylene oxide is converted to ethylene carbonate or ethylene glycol in the absorber.

Towers or columns allowing the intimate gas-liquid contacting required for such absorption are well known in the art and are referred to, for example, as fractionation, distillation or absorption towers. Such towers or columns contain trays stacked vertically through the column and are designed to conduct liquids in a zig-zag course downwardly through the column while admitting gases upwardly into horizontal-flowing portions of the liquid for intimate contact with the liquid.

Trays for providing the horizontal flow of the liquid are well known in the art and have been widely used. A tray generally comprises a perforated gas-liquid contacting member or members for effecting intimate contact between a gas rising through the tray and a liquid flowing across the surface of the tray across the perforated member. The perforated gas-liquid contacting member is in some instances provided with bubble caps or valves. At one edge of the contacting member of the tray is a liquid inlet area for receiving the liquid onto the tray. This area will generally contain no perforations. At the opposite edge of the contacting member is the liquid discharge end or region of the tray, which is provided with an outlet weir member extending vertically above the surface of the tray. The flowing liquid overflows the outlet weir for discharge from the tray. Accordingly, this outlet weir, maintains a given liquid depth on the tray.

Extending below the trays is one or more downcomer element which, in cooperation with the inner surface of wall of column or tower, forms a downcomer for the passage of liquid downwardly from the tray liquid discharge region or end to the liquid inlet region of the vertically adjacent tray directly below. The downwardly flowing liquid received on the liquid inlet region or area then flows across the surface of this tray in a path across the perforated gas-liquid contacting member, to the tray discharge end or region and is discharged from the tray, over the outlet weir into the next downcomer.

A gas flows upwardly in the column through the perforations of the gas-liquid contacting members of the trays, allowing intimate contact with the liquid flowing horizontally across the surface of the tray. The gas is prevented from passing up the downcomers, as the downcomer element also functions as a baffle extending below the surface level of the flowing liquid to seal the downcomers from gas bypass.

However, gas bypassing through downcomers may occur during start up of the process, when the column is not yet sufficiently filled with liquid.

The structure of an individual column and the trays therein must be determined on the basis of the process for which they are intended to be used. For example, outlet weirs in the art vary in height depending on the nature of the operation of the column or tower. U.S. Pat. No. 4,435,595 describes a reactive distillation process for the production of high purity methyl acetate in which high weirs are used. The outlet weirs in this case are 5 inches (12.7 cm) in height.

US 2013/0245318 teaches a rectification column for the production of a methionine salt in which the weirs have a height of 100 mm or more.

EP 1964829 describes a multi-stage distillation column comprising vertically stacked trays having a weir height in the range of from 3 to 20 cm.

The present inventors have sought to provide an improved process for the manufacture of alkylene glycol from an alkene. In particular, the present inventors have sought to provide a process and an absorption system that allows reactive absorption of the gas composition from an alkylene oxide reactor with high selectivity.

SUMMARY OF THE INVENTION

Accordingly, the present invention provides a process for the preparation of an alkylene glycol from an alkene comprising steps of:
(a) supplying a gas composition comprising alkylene oxide, alkene, oxygen, carbon dioxide and water vapour to the bottom of an alkylene oxide absorber, said absorber comprising a column of vertically stacked trays, wherein each of the vertically stacked trays comprises a perforated gas-liquid contacting member or members, a liquid inlet area, an outlet weir extending vertically above the surface of the tray at the opposite end of the tray from the liquid inlet area and a downcomer element which, in cooperation with the inner surface of wall of the column, forms a downcomer for the passage of liquid downwardly to the liquid inlet region of the vertically adjacent tray directly below, wherein the outlet weir on each tray is at least 200 mm and at most 1500 mm in height and allowing the gas composition to pass upwards through the column;
(b) supplying lean absorbent to the top of the alkylene oxide absorber and allowing the lean absorbent to pass downwards through the column; and
(c) intimately contacting the gas composition with lean absorbent on the trays in the alkylene oxide absorber in the presence of one or more catalysts that promote carboxylation and hydrolysis; and
(d) withdrawing fat absorbent from the alkylene oxide absorber.

The present invention also provides an absorber apparatus for the reactive absorption of a gas composition comprising alkylene oxide, alkene, oxygen, carbon dioxide and water vapour comprising a column containing vertically stacked trays, with an inlet for liquid lean absorbent at the top of the column, an inlet for the gas composition at the bottom of the column above a sump, an outlet for fat absorbent at the bottom of the column and an outlet for unabsorbed gas at the top of the column, wherein each of the vertically stacked trays comprises a perforated gas-liquid contacting member or members, a liquid inlet area, an outlet weir at the opposite end of the tray from the liquid inlet area extending vertically above the surface of the tray and a downcomer element which, in cooperation with the inner surface of wall of the column, forms a downcomer for the passage of liquid downwardly to the liquid inlet region of the vertically adjacent tray directly below and wherein the outlet weir on each tray is at least 250 mm, preferably at least 350 mm and at most 1500 mm in height.

BRIEF DESCRIPTION OF THE DRAWINGS

FIG. 1 is a schematic diagrams showing an exemplary, but non-limiting embodiment of the invention.

DETAILED DESCRIPTION OF THE INVENTION

The present invention provides a process and an apparatus for the preparation of an alkylene glycol.

Alkylene glycols are generally produced from the corresponding alkylene as set out below:

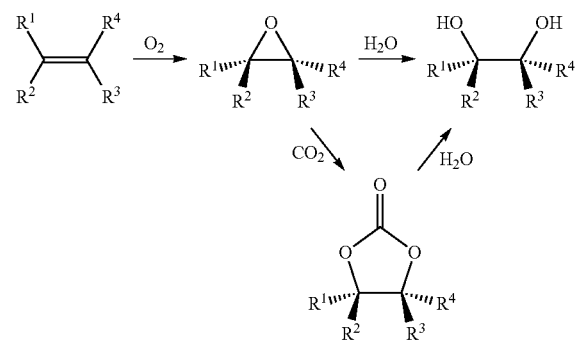

$R^1$, $R^2$, $R^3$ and $R^4$ are preferably chosen from hydrogen or an optionally substituted alkyl group having from 1 to 6 carbon atoms, more preferably from 1 to 3 carbon atoms. As substituents, moieties such as hydroxy groups may be present. Preferably, $R^1$, $R^2$ and $R^3$ represent hydrogen atoms and $R^4$ represents hydrogen or a non-substituted $C_1$-$C_3$-alkyl group and, more preferably, $R^1$, $R^2$, $R^3$ and $R^4$ all represent hydrogen atoms.

Examples of suitable alkylene glycols therefore include ethylene glycol and propylene glycol. In the present invention the most preferred alkylene glycol is ethylene glycol.

In the present invention, the gas composition comprising alkylene oxide, alkene, oxygen, carbon dioxide and water vapour is preferably derived from the reactor product of an alkylene oxide reactor, in which an alkene is reacted with oxygen in the presence of a catalyst in a reactor to form alkylene oxide. In such a reaction, the oxygen may be supplied as oxygen or as air, but is preferably supplied as oxygen. Ballast gas, for example methane or nitrogen, is typically supplied to allow operation at high oxygen levels without causing a flammable mixture. Moderator, e.g. monochloroethane or dichloroethane, may be supplied for ethylene oxide catalyst performance control. The alkene, oxygen, ballast gas and moderator are preferably supplied to recycle gas that is supplied to the alkylene oxide reactor from the alkylene oxide absorber (optionally via a carbon dioxide absorption column).

The alkylene oxide reactor is typically a multitubular, fixed bed reactor. The catalyst is preferably finely dispersed silver and optionally promoter metals on a support material, for example, alumina. The reaction is preferably carried out at pressures of greater than 1 MPa and less than 3 MPa and temperatures of greater than 200° C. and less than 300° C.

The gas composition from the alkylene oxide reactor is preferably cooled in one or more coolers, preferably with generation of steam at one or more temperature levels.

The gas composition comprising alkylene oxide, alkene, oxygen, carbon dioxide and water vapour is supplied to an alkylene oxide absorber comprising a column of vertically stacked trays. The trays provide a surface area for the absorbent and gas composition to come into contact, facilitating mass transfer between the two phases. Additionally, trays provide considerable liquid volume in which the liquid phase reaction can occur.

Each of the vertically stacked trays in the column comprises a perforated gas-liquid contacting member or members, a liquid inlet area, an outlet weir extending vertically above the surface of the tray at the opposite end of the tray from the liquid inlet area and a downcomer element. The downcomer element, in cooperation with the inner surface of wall of the column, forms a downcomer for the passage of liquid downwardly to the liquid inlet region of the vertically adjacent tray directly below. In embodiments of the invention wherein the column is of a large size, there may be more than one liquid inlet area, more than one outlet weir and more than one downcomer element per tray. The singular term 'a' or 'an' has been used throughout this text for clarity. However, in this instance, the term 'a liquid inlet area' refers to one or more liquid inlet area, the term 'an outlet weir' refers to one or more outlet weir and the term 'a downcomer element' refers to one or more downcomer element.

The reaction speed of the reactive absorption process for the conversion of alkylene oxide to alkylene glycol is relatively slow and, therefore, requires a large liquid hold up within the absorption column. The present inventors have discovered that this can be achieved by using exceptionally tall outlet weirs, in the process and apparatus of the invention. Such a feature provides a reduced column size and an efficient process and reduces both CAPEX and OPEX while still maintaining high selectivity (>95%) for the production of MEG.

In the present invention, the outlet weir on each tray is preferably at least 250 mm, more preferably at least 350 mm, even more preferably at least 400, yet even more preferably at least 500, most preferably at least 600 mm in height. The outlet weirs are at most 1500 mm in height, preferably at most 1000 mm, more preferably at most 800 mm in height.

The distance between two consecutive trays in a column is termed the plate spacing. The space between the top of a weir and the tray directly above it, termed 'vapour space' herein, can be calculated as the plate spacing minus the weir height and is preferably at least 150 mm, more preferably at least 200 mm. The vapour space is preferably no more than 1000 mm, more preferably no more than 500 mm.

In all embodiments of the invention the gas composition is supplied to the bottom of the column and passes upwards through the trays. The gas composition is preferably supplied below the bottom tray in the column. Liquid lean absorbent is supplied at or near to the top of the absorber and the liquid flows downwards from tray to tray. The lean absorbent is preferably supplied to the uppermost tray in the absorption column. In another embodiment, the lean absorbent is supplied such that there are trays above the point at which the lean absorbent is supplied to the alkylene oxide absorber. In this embodiment, cold water or additional lean absorbent that has been cooled can be supplied at the top of the alkylene oxide absorber to absorb alkylene oxide or contaminants in the top of the alkylene oxide absorber.

The number of trays present in the column will be dependent on the weir height and the amount of liquid hold up required in the column. Preferably, the column comprises at least 20 trays, more preferably at least 30 trays. Preferably the column comprises less than 100 trays, more preferably less than 70 trays, most preferably less than 50 trays. More trays increase the absorption ability and reaction volume of the column for any given weir height, but adding additional trays increase the size of the column and therefore increase the expense involved in building and running it.

In a particularly preferred embodiment of the invention, each of the outlet weirs is provided with one or more apertures positioned below the upper edge of said outlet weir and in a position or positions that would be completely below the surface of the lean absorbent on the tray during normal operation. Preferably, the apertures are present in the bottom half of each outlet weir.

Normal operation is defined herein as operation wherein the trays are all full and at least 90% of the liquid flowing down through the column is flowing over the weir rather than through the apertures.

In the embodiment wherein apertures are present in the outlet weirs, they are designed such that during normal operation less than 10% of the total liquid flow is passing through the apertures. Preferably no more than 20%, more preferably no more than 10%, even more preferably no more than 5%, most preferably no more than 2%, of the surface area of each outlet weir is taken up with the one or more apertures. In one preferred embodiment of the invention the weir height is in the range of from 250 mm, more preferably from 350 mm to 1000 mm and the aperture area (in mm$^2$/tray) is in the range of from 10 to 20 times the process flow rate (in m$^3$/hr).

This embodiment provides the advantage of a smoother start up process. In a start up process, as liquid (lean absorbent) is fed into the column, it will start to fill trays starting from the point at which it is fed and flowing downwards. Until each tray is filled past the point wherein the downcomer element from the tray above reaches below the level of the liquid on the tray, gas supplied to the column will be able to pass upwards through the column through the empty downcomers, bypassing the liquid. Such a problem will be exacerbated with high weirs. The use of apertures in the outlet weirs allows the column to fill smoothly on start up and shortens the time required to achieve effective operation of the column.

The gas composition is intimately contacted with lean absorbent on the trays in the alkylene oxide absorber in the presence of one or more catalysts that promote carboxylation and hydrolysis. If this occurs in the presence of only one catalyst, then the catalyst must promote carboxylation and hydrolysis. If this occurs in the presence of two or more catalysts, then each catalyst can promote carboxylation or hydrolysis or can promote both reactions (provided that at least one catalyst promotes carboxylation and at least one catalyst promotes hydrolysis). In a preferred embodiment the gas composition is contacted with lean absorbent in the presence of at least two catalysts including a first catalyst that promotes carboxylation and a second catalyst that promotes hydrolysis.

In one embodiment of the invention, the one or more catalysts that promote carboxylation and hydrolysis is/are homogeneous, and the lean absorbent comprises the one or more catalysts. Homogeneous catalysts that are known to promote carboxylation include alkali metal halides such as potassium iodide and potassium bromide, and halogenated organic phosphonium or ammonium salts such as tributyl-methylphosphonium iodide, tetrabutylphosphonium iodide, triphenylmethylphosphonium iodide, triphenyl-propylphosphonium bromide, triphenylbenzylphosphonium chloride, tetraethylammonium bromide, tetramethylammonium bromide, benzyltriethylammonium bromide, tetrabutylammonium bromide and tributylmethylammonium iodide. Homogeneous catalysts that are known to promote hydrolysis include basic alkali metal salts such as potassium carbonate, potassium hydroxide and potassium bicarbonate, or alkali metal metalates such as potassium molybdate. Preferred homogeneous catalyst systems include a combination of potassium iodide and potassium carbonate, and a combination of potassium iodide and potassium molybdate.

In another embodiment of the invention, the one or more catalysts that promote carboxylation and hydrolysis is/are heterogeneous and the heterogeneous catalyst(s) are contained in the vertically stacked trays. Heterogeneous catalysts that promote carboxylation include quaternary ammonium and quaternary phosphonium halides immobilized on silica, quaternary ammonium and quaternary phosphonium halides bound to insoluble polystyrene beads, and metal salts such as zinc salts immobilised on solid supports containing quaternary ammonium or quaternary phosphonium groups, such as ion exchange resins containing quaternary ammonium or quaternary phosphonium groups. Heterogeneous catalysts that promote hydrolysis include metalates immobilised on solid supports, for example molybdates, vanadates or tungstates immobilised on ion exchange resins containing quaternary ammonium or quaternary phosphonium groups, or basic anions such as bicarbonate ions immobilised on solid supports, for example bicarbonate immobilised on ion exchange resins containing quaternary ammonium or quaternary phosphonium groups.

In the embodiment wherein the gas composition is contacted with lean absorbent in the presence of at least two catalysts including a first catalyst that promotes carboxylation and a second catalyst that promotes hydrolysis, the ratio of first catalyst to second catalyst can be adjusted in order to vary the amount of carbon dioxide that is consumed or released in the alkylene oxide absorber. Preferably the gases from the alkylene oxide absorber are partially or entirely supplied to a carbon dioxide absorption column wherein the carbon dioxide is at least partially absorbed by a recirculating absorbent stream. By controlling the amount of carbon dioxide that is consumed or released in the alkylene oxide absorber, the capacity and cost of a carbon dioxide absorber column can be reduced.

The lean absorbent comprises at least 5 wt % water. The water that is present in the lean absorbent is used in the hydrolysis of alkylene oxide and alkylene carbonate that occurs in the alkylene oxide absorber. Preferably, the lean absorbent comprises at least 10 wt % water, more preferably at least 15 wt % water, most preferably at least 20 wt % water. Preferably the lean absorbent comprises less than 80 wt % water, more preferably no more than 50 wt % water, even more preferably no more than 30 wt % water. Higher levels of water in the lean absorbent may still provide good selectivity and catalyst performance, but higher quantities of water require additional water removal, with associated energy and equipment costs. The lean absorbent may also comprise alkylene glycol.

The temperature in the alkylene oxide absorber is preferably from 50° C. to 160° C., preferably from 80° C. to 150° C., more preferably from 80 to 120° C. This is higher than the temperature in an absorber in a conventional process and is required to promote the carboxylation and hydrolysis reactions. Temperature higher than 160° C. is not preferred as this may reduce the selectivity of the alkylene oxide conversion to alkylene glycol. Both the gas composition comprising alkylene oxide, alkene, oxygen, carbon dioxide and water vapour and the lean absorbent are preferably supplied to the alkylene oxide absorber at temperatures in the range from 50° C. to 160° C.

The pressure in the alkylene oxide absorber is from 1 to 4 MPa, preferably from 2 to 3 MPa. The preferred pressure is a compromise between lower pressures that require less expensive equipment (e.g. equipment having thinner walls) and higher pressures that increase absorption and reduce the volumetric flow of the gas, thereby reducing the size of equipment and piping.

At least 50% of the alkylene oxide entering the alkylene oxide absorber is converted in the alkylene oxide absorber. Preferably, at least 60%, more preferably at least 70%, even more preferably at least 80%, most preferably at least 90% of the alkylene oxide entering the alkylene oxide absorber is converted in the alkylene oxide absorber. The alkylene oxide may undergo carboxylation, providing alkylene carbonate. The alkylene oxide may undergo hydrolysis, providing alkylene glycol. Additionally, the alkylene carbonate that is produced from the alkylene oxide may undergo hydrolysis, providing alkylene glycol.

Preferably, in the present invention, the alkylene absorber forms part of a reaction system and process for the production, isolation and purification of alkylene glycol from alkylene via the corresponding alkylene oxide such as those described in EP 2178815 and similar. It will readily be understood that the absorber will be integrated into such a system which will contain a number of reactor vessels, columns and recycle streams.

The gas composition comprising alkylene oxide, alkene, oxygen, carbon dioxide and water vapour that is supplied to the alkylene oxide absorber comprises carbon dioxide. It is possible that the gas composition may contain insufficient carbon dioxide to achieve desired levels of carboxylation. An additional source of carbon dioxide is preferably supplied to the alkylene oxide absorber, e.g. recycle carbon dioxide from a finishing reactor, carbon dioxide from a carbon dioxide recovery unit or, at start-up, carbon dioxide from an external source. The ratio of the total amount of carbon dioxide supplied to the alkylene oxide absorber to the amount of alkylene oxide supplied to the alkylene oxide absorber is preferably between 5:1 and 1:3, more preferably between 3:1 and 4:5. A higher quantity of carbon dioxide improves the selectivity of the process because most alkylene oxide reacts with carbon dioxide to alkylene carbonate, which is subsequently hydrolysed to alkylene glycol and there is less opportunity for reaction between alkylene oxide and alkylene glycol to produce higher glycols. However, a higher quantity of carbon dioxide may also require additional removal capacity for carbon dioxide in the process and may also lead to a higher level of by-product formation. Alternatively, operating a connected alkylene oxide reactor with a recycled gas stream containing the excess carbon dioxide may adversely affects the catalyst performance.

Gases that are not absorbed in the alkylene oxide absorber are preferably partially or entirely supplied to a carbon dioxide absorption column wherein the carbon dioxide is at least partially absorbed by a recirculating absorbent stream. Gases that are not absorbed by the recirculating absorbent stream are preferably recombined with any gases bypassing the carbon dioxide absorption column and are recycled to the alkylene oxide reactor. Preferably the gases are cooled prior to recycle to the alkylene oxide reactor in order to reduce the water content. The water removed from the gas stream can optionally be recirculated to the alkylene oxide absorber.

The performance of the catalyst in the alkylene oxide reactor may be detrimentally affected by an excess of water.

If the one or more catalysts that promote carboxylation and hydrolysis include a halogen-containing catalyst (e.g. an alkali metal halide, a halogenated organic phosphonium or ammonium salt or a quaternary ammonium or quaternary phosphonium halide immobilized on a solid support), then gases that are recycled from the alkylene oxide absorber to the alkylene oxide reactor may comprise halide-containing impurities such as iodide-containing impurities or bromide-containing impurities. It is possible that the catalyst in the alkylene oxide reactor may be detrimentally affected by these impurities. Therefore, in this embodiment it is preferred that gases that are recycled from the alkylene oxide absorber to the alkylene oxide reactor are contacted with one or more purification adsorbents capable of reducing the quantity of halide-containing impurities (especially iodide-containing impurities or bromide-containing impurities) prior to contacting the catalyst in the alkylene oxide reactor. The one or more purification adsorbent may be located within the reactor tubes of the alkylene oxide reactor, within the alkylene oxide reactor upstream from the reactor tubes or separately upstream from the alkylene oxide reactor.

Fat absorbent is withdrawn from the alkylene oxide absorber, preferably by withdrawing liquid from the bottom of the alkylene oxide absorber, i.e. below the vertically stacked trays.

In one embodiment of the invention, a portion or all of the fat absorbent from step (d) is subsequently supplied to one or more finishing reactors. Such finishing reactors may include reactors suitable for carboxylation and/or reactors suitable for hydrolysis and/or reactors suitable for hydrolysis and carboxylation. Supply to one or more finishing reactors is preferred if a significant quantity (e.g. at least 1%) of alkylene oxide or alkylene carbonate is not converted to alkylene glycol in the alkylene oxide absorber. Conversely, if the majority (e.g. greater than 90%) of alkylene oxide and alkylene carbonate is converted to alkylene glycol in the alkylene oxide absorber, then one or more finishing reactors may not be required and the equipment used in the process is thereby reduced. To maximise conversion of alkylene oxide in the alkylene oxide absorber, spraying nozzles can be employed in the sump (bottom section) of the alkylene oxide absorber, to disperse carbon dioxide and promote carboxylation. Optionally, steam may be injected into a finishing reactor suitable for hydrolysis.

Carbon dioxide may be produced in the one or more finishing reactors and is preferably separated from the product stream as it leaves the one or more finishing reactors and is optionally recycled to the reactive absorber.

The temperature in the one or more finishing reactors is typically from 100 to 200° C., preferably from 100 to 180° C. The pressure in the one or more finishing reactors is typically from 0.1 to 3 MPa.

The fat absorbent from step (d) or a product stream from at least one of the one or more finishing reactors is optionally supplied to a flash vessel or to a light ends stripper. Light ends are removed in the flash vessel or in the light ends stripper. (Light ends are gases such as the alkene, and also ballast gases such as methane, that are present in the gas composition comprising alkylene oxide, alkene, oxygen, carbon dioxide and water vapour and are absorbed into the absorbent in step (c)).

A flash vessel may be located directly after the alkylene oxide absorber so the fat absorbent passes directly from step (d) to the flash vessel. When there is at least one finishing reactor, a flash vessel may be located after all of the one or more finishing reactors so that the product stream passes from said finishing reactors to the flash vessel. When there is more than one finishing reactor, a flash vessel may be located between the finishing reactors such that the fat absorbent passes from step (d) to at least one finishing reactor, then the product stream passes to the flash vessel and then the stream from the flash vessel passes to at least another finishing reactor.

The flash can be at pressure from 0.01 to 2 MPa, preferably from 0.1 to 1 MPa, most preferably from 0.1 to 0.5 MPa.

Fat absorbent from step (d) or the product stream from the finishing reactors or other product stream comprising alkylene glycol is supplied to a dehydrator. The stream that is supplied to the dehydrator preferably comprises very little alkylene oxide or alkylene carbonate, i.e. most of the alkylene oxide or alkylene carbonate has been converted to alkylene glycol prior to supply to the dehydrator column, either in the alkylene oxide absorber or in a finishing reactor. Preferably the molar ratio of alkylene glycol to alkylene oxide and alkylene carbonate (combined) in the stream supplied to the dehydrator column is greater than 90:10, more preferably greater than 95:5, most preferably greater than 99:1.

The dehydrator is preferably one or more columns, including at least one vacuum column, preferably operating at a pressure of less than 0.05 MPa, more preferably less than 0.025 MPa and most preferably about 0.0125 MPa.

The dehydrated product stream is purified to remove impurities and provide a purified alkylene glycol product stream. If the one or more catalysts are homogeneous catalysts, it will be necessary to separate the one or more catalysts from the dehydrated product stream, preferably in a flash vessel. The one or more homogeneous catalysts are preferably recombined with the lean absorbent and supplied to the alkylene oxide absorber.

DETAILED DESCRIPTION OF THE DRAWINGS

FIG. 1 illustrates an embodiment of the present invention. It shows a section 1 of an absorption column. It should be noted that a small number of trays are illustrated in this FIGURE and that the top of the uppermost tray and the bottom of the lowermost tray are not shown.

The column consists of a number of vertically stacked trays 2. Each tray 2 comprises a perforated gas-liquid contacting member 3, a liquid inlet area 4 and an outlet weir 5 extending vertically above the surface of the tray 2 at the opposite end from the liquid inlet area.

A downcomer element 6 extends below each tray and, in cooperation with the inner surface of the wall of the column, forms a downcomer 7 for the passage of liquid downwards to the liquid inlet region directly below.

In operation, the gas composition (illustrated by arrows 8) moves upwards through the perforated gas-liquid contacting members. The liquid 9 fills the trays and passes over the outlet weirs 5 as illustrated by the arrows 10.

Apertures (11) may be provided in each outlet weir below the upper edge of said outlet weir.

That which is claimed is:

1. A process for the preparation of an alkylene glycol from an alkene comprising:
(a) supplying a gas composition comprising alkylene oxide, alkene, oxygen, carbon dioxide and water vapour to the bottom of an alkylene oxide absorber that comprises a column of vertically stacked trays, wherein each of the vertically stacked trays comprises:

a perforated gas-liquid contacting member or members,
a liquid inlet area,
an outlet weir extending vertically above a surface of the tray at an opposite end of the tray from the liquid inlet area and having a height of at least 200 mm and at most 1500 mm, and
a downcomer element which, in cooperation with an inner surface of a wall of the column, forms a downcomer for the passage of liquid downwardly to the liquid inlet area of an adjacent vertically stacked tray below, and
allowing the gas composition to pass upwards through the alkylene oxide absorber;
(b) supplying lean absorbent to the top of the alkylene oxide absorber and allowing the lean absorbent to pass downwards through the alkylene oxide absorber;
(c) intimately contacting the gas composition with lean absorbent on the trays in the alkylene oxide absorber in the presence of one or more catalysts that promote carboxylation and hydrolysis; and
(d) withdrawing fat absorbent from the alkylene oxide absorber.

2. The process as claimed in claim 1, wherein the outlet weir on each vertically stacked tray has a height of at least 250 mm and at most 1000 mm.

3. The process as claimed in claim 1, wherein the outlet weir on each vertically stacked tray comprises one or more apertures positioned below an upper edge of the outlet weir.

4. The process according to claim 1, wherein the one or more catalyst that promote carboxylation and hydrolysis are selected from the group consisting of alkali metal halides, basic alkali metal salts and combinations thereof.

5. The process as claimed in claim 1, wherein the lean absorbent comprises at least 5 wt % and less than 80 wt % water.

* * * * *